United States Patent [19]

Wada et al.

[11] Patent Number: 5,021,589

[45] Date of Patent: * Jun. 4, 1991

[54] METHOD FOR PRODUCING A LACTONE

[75] Inventors: Keisuke Wada, Yokohama; Yoshinori Hara, Machida; Koushi Sasaki, Kawasaki, all of Japan

[73] Assignee: Mitsubishi Kasei Corporation, Tokyo, Japan

[ * ] Notice: The portion of the term of this patent subsequent to Jan. 9, 2007 has been disclaimed.

[21] Appl. No.: 428,785

[22] Filed: Oct. 30, 1989

Related U.S. Application Data

[62] Division of Ser. No. 72,744, Jul. 13, 1987, Pat. No. 4,892,955.

[30] Foreign Application Priority Data

Aug. 19, 1986 [JP] Japan .................................. 61-193691
Apr. 18, 1987 [JP] Japan .................................. 62-95681

[51] Int. Cl.$^5$ ............................................. C07D 307/26
[52] U.S. Cl. ..................................... 549/325; 549/326
[58] Field of Search ............................... 549/325, 326

[56] References Cited

U.S. PATENT DOCUMENTS 4,415,740 11/1983 Kaufman .............................. 549/323
4,892,955 1/1990 Wada et al. ........................ 549/325

Primary Examiner—Frederick E. Waddell
Assistant Examiner—Ba K. Trinh
Attorney, Agent, or Firm—Oblon, Spivak, McClelland, Maier & Neustadt

[57] ABSTRACT

A method for producing a lactone by hydrogenating a dicarboxylic acid, a dicarboxylic acid anhydride and/or a dicarboxylic acid ester in the presence of a catalyst, wherein said catalyst is a ruthenium catalyst comprising (1) ruthenium, (2) an organic phosphine and (3) a conjugate base of an acid having a pKa of less than 2.

7 Claims, No Drawings

METHOD FOR PRODUCING A LACTONE

This is a division, of U.S. application Ser. No. 07/072,744, filed on July 13, 1987, now U.S. Pat. No. 4,892,955.

FIELD OF THE INVENTION

The present invention relates to a method for producing a lactone by hydrogenating a dicarboxylic acid, a dicarboxylic acid anhydride and/or a dicarboxylic acid ester.

DISCUSSION OF BACKGROUND

A method for producing a lactone by hydrogenating a dicarboxylic acid, a dicarboxylic acid anhydride and/or a dicarboxylic acid ester, has been studied since long ago, and various catalysts have been proposed.

For example, many proposals have been made on a process for producing a lactone by a fixed bed or liquid phase or suspension phase hydrogenation reaction system by using e.g. a nickel-type catalyst (e.g. Japanese Examined Patent Publication No. 6947/1968), a cobalt-type catalyst (e.g. Japanese Unexamined Patent Publication No. 95057/1976), a copper-chromium-type catalyst (e.g. Japanese Examined Patent Publication No. 20119/1963) and a copper-zinc-type catalyst (e.g. Japanese Examined Patent Publication No. 14463/1967). On the other hand, it is also known to produce a lactone by conducting the above-mentioned hydrogenation reaction by using a ruthenium catalyst for a homogeneous system. For example, U.S. Pat. No. 3,957,827 discloses a hydrogenation reaction under a condition of from 40 to 400 psi by using a catalyst of $[RuX_n(PR_1R_2R_3)_xL_y]$ type. U.S. Pat. No. 4,485,246 discloses that a hydrogenation reaction by means of a similar catalyst is conducted in the presence of an organic amine. Further, U.S. Pat. No. 4,485,245 discloses a hydrogenation reaction by means of a catalyst of $[Ru_mX_n(SnCl_2)(MR_3)_nL_y]$ type.

However, such conventional methods wherein the nickeltype catalyst, the cobalt-type catalyst, the copper-chromium-type catalyst and the copper-zinc-type catalyst was used, all had a problem that it was necessary to employ a severe condition of a few tens atm. or higher. On the other hand, the conventional method wherein a ruthenium catalyst for a homogeneous system was used, had not only a drawback that the catalytic activity was slightly low, but also fatal problems that the catalytically useful life was extremely short, and the reactor was likely to be corroded by the use of halogen, although the method has a feature that the hydrogenation reaction proceeds under a relatively mild condition.

SUMMARY OF THE INVENTION

It is an object of the present invention to overcome the above-mentioned conventional problems and to provide a method for producing a lactone whereby a dicarboxylic acid, a dicarboxylic acid anhydride and/or a dicarboxylic acid ester can be hydrogenated industrially more advantageously than ever.

The present inventors have conducted extensive research to accomplish the above object, and as a result, have found that in a method for producing a lactone by hydrogenating a dicarboxylic acid, a dicarboxylic acid anhydride and/or a dicarboxylic acid ester, if a ruthenium catalyst comprising (1) ruthenium, (2) an organic phosphine and (3) a conjugate base of an acid having a pKa of less than 2, is used as the catalyst, not only the catalytic activity for hydrogenation increases, but also the stability in the activity of the catalyst can be improved. The present invention has been accomplished on the basis of this discovery.

The present invention provides a method for producing a lactone by hydrogenating a dicarboxylic acid, a dicarboxylic acid anhydride and/or a dicarboxylic acid ester in the presence of a catalyst, wherein said catalyst is a ruthenium catalyst comprising (1) ruthenium, (2) an organic phosphine and (3) a conjugate base of an acid having a pKa of less than 2.

DETAILED DESCRIPTION OF THE PREFERRED EMBODIMENTS

Now, the present invention will be described in detail.

The dicarboxylic acid, the dicarboxylic anhydride or a dicarboxylic acid ester used as a starting material of the present invention, is a saturated or unsaturated dicarboxylic acid derivative having from 3 to 7 carbon atoms. As the ester, an alkyl ester is preferred. Particularly preferred as the carboxylic acid base structure, is a derivative having 4 carbon atoms. Specifically, for example, fumaric acid, succinic acid, maleic anhydride, succinic anhydride, dimethyl maleate, diethyl fumarate, di-n-butyl succinate, monomethyl succinate, or monomethyl maleate, may be mentioned.

The catalyst used in the method of the present invention is a ruthenium catalyst comprising (1) ruthenium, (2) an organic phosphine and (3) a conjugate base of an acid having a pKa of less than 2. Preferably, such a ruthenium catalyst further contains (4) a neutral ligand.

Here, the ruthenium (1) may be used in the form of metal ruthenium or a ruthenium compound. As the ruthenium compound, an oxide, hydroxide, inorganic acid salt, organic acid salt or complex compound of ruthenium may be used. Specifically, there may be mentioned ruthenium dioxide, ruthenium tetraoxide, ruthenium dihydroxide, ruthenium chloride, ruthenium bromide, ruthenium iodide, ruthenium nitrate, ruthenium acetate, tris(acetylacetone)ruthenium, sodium hexachlororuthenate, dipotassium tetracarbonylruthenate, pentacarbonylruthenium, cyclopentadienyldicarbonylruthenium, dibromotricarbonylruthenium, chlorotris(triphenylphosphine)hydridoruthenium, bis(tri-n-butylphosphine)tricarbonylruthenium, dodecacarbonyltriruthenium, tetrahydridedecacarbonyltetraruthenium, dicesium octadecacarbonylhexaruthenate, tetraphenylphosphonium undecacarbonylhydridetriruthenate.

Such metal ruthenium or ruthenium compound is used in an amount such that the concentration in the reaction solution will be 0.0001 to 100 mol, preferably from 0.001 to 10 mol, as ruthenium in one liter of the reaction solution.

In the method of the present invention, it is necessary to use the organic phosphine (2) together with the ruthenium (1). The organic phosphine is considered to contribute to the control of the electron state of ruthenium or to the stabilization of the activity of ruthenium. Specific examples of such an organic phosphine include a trialkylphosphine such as tri-n-butylphosphine or dimethyl-n-octylphosphine, a tricycloalkylphosphine such as tricyclohexylphosphine, a triarylphosphine such as triphenylphosphine, an alkylarylphosphine such as dimethylphenylphosphine, and a polyfunctional phosphine such as 1,2-bis(diphenylphosphino)ethane.

Such as organic phosphine is used in an amount within a range of from 0.1 to 1,000 mol, preferably from 1 to 100 mol, per mol of ruthenium. The organic phosphine may be supplied to the reaction system by itself or in the form of a composite with ruthenium.

By using a conjugate base of an acid having a pKa of less than 2 as an additional accelerator for the ruthenium constituting the main catalyst for the hydrogenation reaction of the present invention, it is possible to have the hydrogenation reaction proceeded under a relatively mild condition by utilizing the merits of the ruthenium as the main component, and it is also possible to improve the catalytic activity for hydrogenation and to improve the stability of the activity and the selectivity for the desired product.

The conjugate base of an acid having a pKa of less than 2 may be any material so long as it is capable of forming such a conjugate base during the preparation of the catalyst or in the reaction system. It may be supplied in the form of a Brønsted acid having a pKa of less than 2, or a salt of such an acid. Specifically, there may be mentioned Brønsted acids including inorganic acids such as nitric acid, perchloric acid, borofluoric acid, hexafluorophosphoric acid and fluorosulfonic acid, and organic acids such as trichloroacetic acid, dichloroacetic acid, trifluoroacetic acid, methanesulfonic acid, dodecylsulfonic acid, octadecylsulfonic acid, trifluoromethanesulfonic acid, benzenesulfonic acid, p-toluenesulfonic acid and a sulfonated styrene-divinylbenzene copolymer, or alkali metal salts, alkaline earth metal salts, ammonium salts or silver salts of these Brønsted acids.

It may be added in the form of an acid derivative which is capable of forming such a conjugate base in the reaction system. For example, it may be added in the form of an acid halide, an acid anhydride, an ester or an acid amide to the reaction system to obtain similar effects.

Such an acid or base is used in an amount within a range of from 0.01 to 1,000 mol, preferably from 0.1 to 100 mol, relative to ruthenium.

The ruthenium catalyst of the present invention may further contain a neutral ligand. Such a neutral ligand includes hydrogen; an olefin such as ethylene, propylene, butene, cyclopentene, cyclohexene, butadiene, cyclopentadiene, cyclooctadiene or norbornadiene; an oxygen-containing compound such as carbon monoxide, diethyl ether, anisole, dioxane, tetrahydrofuran, acetone, acetophenone, benzophenone, cyclohexanone, propionic acid, caproic acid, butyric acid, benzoic acid, ethyl acetate, allyl acetate, benzyl benzoate, benzyl stearate or valerolactone; a nitrogen-containing compound such as nitrogen oxide, acetonitrile, propionitrile, benzonitrile, cyclohexyl isonitrile, butylamine, aniline, toluidine, triethylamine, pyrrole, pyridine, N-methylformamide, acetamide, 1,1,3,3-tetramethyl urea, N-methylpyrrolidone, caprolactam or nitromethane; a sulfur-containing compound such as carbondisulfide, n-butylmercaptan, thiophenol, dimethylsulfide, dimethyldisulfide, thiophene, dimethylsulfoxide or diphenyl sulfoxide; and a phosphorus-containing compound other than an organic phosphine, such as tributylphosphine oxide, ethyldiphenylphosphine oxide, triphenylphosphine oxide, diethylphenyl phosphinate, diphenylethyl phosphinate, diphenylmethyl phosphonate, O,O-dimethylmethyl phosphonothiorate, triethyl phosphite, triphenyl phosphite, triethyl phosphate, triphenyl phosphate or hexamethylphosphoric triamide. The present invention includes a case wherein a starting material for the reaction, a reaction product or a solvent for the reaction serves as a neutral ligand.

The ruthenium catalyst to be used in the method of the present invention, may preliminarily be prepared and isolated for use (e.g. J. Organometal. Chem. 77 C-31 ('74)). Otherwise, its precursor may be added to the reaction system so that the ruthenium catalyst is prepared in the reaction system.

The ruthenium catalyst of the present invention may be prepared, for example, by treating a halogen-containing ruthenium compound such as cyclooctadiene dichlororuthenium or dichlorotristriphenylphosphine ruthenium with a base of e.g. $M^+Y^-$ (wherein M is an alkali metal, an alkaline earth metal, a metal of Group IB, or an onium cation, and Y is a conjugate base of an acid having a pKa of less than 2). (For example, see the formula (1) in Inorg. Chem. 17 1965 ('78))

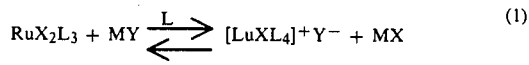

$$RuX_2L_3 + MY \xrightleftharpoons{L} [LuXL_4]^+Y^- + MX \quad (1)$$

wherein X is a halogen such as chlorine or bromine, L is an organic phosphine or a neutral ligand, and M and Y are as defined above.

Otherwise, it may be prepared by a method wherein a Bronsted acid having a pKa of less than 2 or its salt (an onium salt compound such as an ammonium salt, a phosphonium salt, a sulfonium salt or an oxonium salt) is added to a ruthenium hydride compound such as dihydridotetrakis(triphenylphosphine)ruthenium or hydridochlorotris(triphenylphosphine)ruthenium, or to a ruthenium compound capable of forming such a ruthenium hydride compound under the hydrogenation reaction condition (e.g. see the formula (2) in J. Chem. Soc. Dalton Trans. 370 ('75)).

$$RuH_2L_4 + M'Y \rightleftharpoons [RuHL_4]^+Y^- + M'H \quad (2)$$

wherein L and Y are as defined above, and M' is a proton or an onium cation such as an ammonium, phosphonium, sulfonium or oxonium ion.

Further, the catalyst may be prepared by a method wherein a ruthenium hydride compound is treated with a salt of a stable carbenium ion such as triphenylcarbenium ion or tropylium ion (the counter ion being a conjugate salt group of an acid having a pKa of less than 2) (e.g. see the formula (3) in Inorg. Chem. 17 1965 ('78))

$$RuH_2L_4 + Ph_3C^+Y^- \rightleftharpoons [RuHL_4]^+Y^- + Ph_3CH \quad (3)$$

wherein L and Y are as defined above.

The method of the present invention may be conducted in the absence of a solvent i.e. by using the starting material for the reaction as the solvent. However, it is possible to use a solvent other than the starting material for the reaction. Such a solvent includes an ether such as diethyl ether, anisole, tetrahydrofuran, ethylene glycol diemthyl ether or dioxane; a ketone such as acetone, methyl ethyl ketone or acetophenone; an alcohol such as methanol, ethanol, n-butanol, benzylalcohol, phenol, ethylene glycol or diethylene glycol; a carboxylic acid such as formic acid, acetic acid, propionic acid or toluylic acid; an ester such as methyl acetate, n-butyl acetate or benzyl benzoate; an aromatic hydrocarbon such as benzene, toluene, ethylbenzene or tetralin; an aliphatic hydrocarbon such as n-hexane, n-octane or cyclohexane; a halogenated hydrocarbon such as dichloromethane, trichloroethane or chlorobenzene; a nitro compound such as nitromethane or nitrobenzene; a carboxylic acid amide such as N,N-dimethylformamide, N,N-dimethylacetamide or N-methylpyrrolidone; other amide such as hexamethylphosphoric acid treamide or N,N,N',N'-tetraethylsulfamide; a urea such as N,N'-dimethylimidazolidone or N,N,N,N-tetramethylurea; a sulfone such as dimethylsulfone or tetramethylenesulfone; a sulfoxide such as dimethylsulfoxide or diphenylsulfoxide; a lactone such as γ-butyrolactone or ε-caprolactone; an polyether such as tetraglyme (tetraethylene glycol dimethyl ether) or 18-crown-6; a nitrile such as acetonitrile or benzonitrile; and a carbonate such as dimethylcarbonate or ethylene carbonate.

The hydrogenation reaction of the present invention may be conducted by introducing the starting material for the reaction, the catalyst component and, if necessary, a solvent, into the reactor, and supplying hydrogen thereto. The hydrogen may be the one diluted with a gas inert to the reaction, such as nitrogen or carbon dioxide. The reaction is conducted usually at a temperature of from 50° to 250° C., preferably from 100° to 200° C. The hydrogen partial pressure in the reaction system is usually from 0.1 to 100 kg/cm$^2$, preferably from 1 to 10 kg/cm$^2$. It is, of course, possible to conduct the reaction at a lower or higher pressure, but such is not advantageous from the industrial point of view.

The reaction may be conducted either in a batch system or in a continuous system. In the case of a batch system, the required reaction time is usually from 1 to 20 hours.

The desired lactone may be recovered from the reaction solution by a usual separation and purification means such as distillation or extraction. Further, the distillation residue may be recycled to the reaction system as a catalyst component.

Now, the present invention will be described in detail with reference to Examples. However, it should be understood that the present invention is by no means restricted to such specific Examples.

EXAMPLE 1

Into a 70 ml SUS microautoclave, 0.0796 g (Ru: 0.2 mmol) of ruthenium acetylacetonate, 0.74 g (2.0 mmol) of trioctylphosphine and 10 ml of tetraglyme were charged, and heat-treated under an argon atmosphere at 200° C. for 4 hours. The heat-treated catalyst solution was yellow.

This catalyst solution was transferred to a bubble tower type SUS reactor, and 0.105 g (1.0 mmol) of ammonium tetrafluoroborate, 5 ml of tetraglyme and 6.7 g (79 mmol) of γ-butyrolactone were charged. Further, 20.0 g (200 mmol) of succinic anhydride was charged as a starting material for the reaction. While introducing hydrogen gas under a hydrogen pressure of 10 atm. at a rate of 100 NTP liter/hr, the mixture was heated at 200° C. for reaction.

The reaction was conducted for 14 hours while intermittently supplementing the starting material in an amount of 7.5 g every two hours since the starting material decreased by consumption or by evaporation.

The production rate of γ-butyrolactone (hereinafter referred to simply as "GBL") was 36 mmol/hr. By-products of the hydrogenation other than GBL were in a trace amount.

During the reaction, the reaction activity was maintained at a constant level.

The conversion of succinic anhydride was 79.2%, and the selectivity for GBL was almost 100%.

EXAMPLES 2 and 3 and COMPARATIVE EXAMPLE 1

Into a bubble tower type SUS reactor, 0.0796 g (Ru: 0.2 mmol) of ruthenium acetylacetonate, 0.74 g (2.0 mmol) of trioctylphosphine, 20 ml of tetraglyme and an ammonium salt as defined in Table 1 were charged, and 20 ml of tetraglyme and, as the starting material, 20.0 g (200 mmol) of succinic anhydride were charged. While supplying hydrogen gas under normal pressure at a rate of 10 NTP liter/hr, the mixture was heated at 200° C. for 4 hours for reaction. The results are shown in Table 1.

TABLE 1

| | Ammonium salt | | Formed GBL (mmol) | Conversion of succinic anhydride (%) | Selectivity for GBL (%) |
| | Type | Amount (mmol) | | | |
|---|---|---|---|---|---|
| Example 2 | Ammonium hexafluorophosphate | 2.0 | 35.7 | 18.0 | 99.0 |
| Example 3 | Ammonium tetrafluoroborate | 1.0 | 39.3 | 19.7 | 99.2 |
| Comparative Example 1 | — | — | 6.8 | 3.4 | Not measured |

EXAMPLE 4

Into a microautoclave, 0.056 g (Ru: 0.2 mmol) of ruthenium cyclooctadienedichloride, 0.101 g (2.0 mmol) of silver hexafluorophosphate, 0.74 g (2.0 mmol) of trioctylphosphine and 10 ml of tetraglyme were charged, and heat-treated at 200° C. for 2 hours to obtain a catalyst solution.

After filtering off silver chloride formed as a by-product, 10 ml of tetraglyme and, as the starting material for the reaction, 20.0 g (200 mmol) of succinic anhydride were added to the catalyst solution. While introducing hydrogen gas under normal pressure at a rate of 20 NTP liter/hr, the mixture was heated at 200° C. for 4 hours.

As a result, 80.8 mmol (yield: 40.4%) of GBL was obtained.

EXAMPLES 5 to 8

Into a microautoclave, 0.0796 g (Ru: 0.2 mmol) of ruthenium acetylacetonate, 0.74 g (2.0 mmol) of trioctylphosphine, 0.105 g (1.0 mmol) of ammonium tetrafluoroborate and 20 ml of the solvent as identified in Table 2, were charged, and heat-treated under an argon atmosphere at 200° C. for 2 hours. Then, 20.0 g (200 mmol) of succinic anhydride was added thereto, and the same hydrogenation reaction as in Example 4 was conducted.

The results are shown in Table 2.

TABLE 2

| | Solvent | Formed GBL (mmol) | Yield of GBL (%) |
|---|---|---|---|
| Example 5 | Tetraglyme | 56.0 | 28.0 |
| Example 6 | Dodecylic acid | 26.7 | 13.4 |
| Example 7 | Dodecyl alcohol | 27.3 | 13.7 |
| Example 8 | 4-Phenylphenol | 19.1 | 9.6 |

EXAMPLES 9 to 12

Into a microautoclave, 0.056 g (0.2 mmol) of ruthenium cyclooctadienedichloride, a silver salt as identified in Table 3, 0.525 g (2.0 mmol) of triphenylphosphine and 10 ml of tetraglyme were charged, and heat-treated under an argon atmosphere at 170° C. for 2 hours to obtain a catalyst solution.

After filtering off formed silver chloride, 10 ml of tetraglyme and 20 g (200 mmol) of succinic anhydride were added to this catalyst solution. While supplying hydrogen gas under normal pressure at a rate of 20 NTP liter/hr, the mixture was heated at 170° C. for 4 hours.

The results of the reaction are shown in Table 3. In each case, hydrogenation by-products other than GBL were in a trace amount.

TABLE 3

| | Silver salt | | Formed GBL (mmol) | Yield of GBL (%) |
|---|---|---|---|---|
| | Type | Amount (mmol) | | |
| Example 9 | Silver p-toluene-sulfonate | 0.4 | 36.8 | 18.4 |
| Example 10 | Silver hexafluoro-phosphate | 0.4 | 33.6 | 16.8 |
| Example 11 | Silver trifluoro-methane-sulfonate | 0.4 | 28.8 | 14.4 |
| Example 12 | Silver nitrate | 0.4 | 27.2 | 13.6 |

COMPARATIVE EXAMPLE 2

The hydrogenation reaction was conducted under the same condition as in Example 5 by using as the catalyst 0.191 g (0.2 mmol) of tristriphenylphosphine dichlororuthenium and 0.368 g (1.4 mmol) of triphenylphosphine, whereby formed GBL was 16.8 mmol (yield: 8.4%).

EXAMPLE 13

Into a 70 ml SUS microautoclave, 0.0199 g (Ru: 0.05 mmol), 0.185 g (0.5 mmol) of trioctylphosphine, 0.084 g (0.44 mmol) of p-toluenesulfonic acid and 16 ml of tetraglyme were charged, and heat-treated under an argon atmosphere at 200° C. for 2 hours to obtain a catalyst solution. To this catalyst solution, 4 g (40 mmol) of succinic anhydride was charged as the starting material for the reaction. While introducing hydrogen at room temperature under 30 atm., the mixture was heated at 200° C. for 2 hours for reaction.

Then, the autoclave was opened, and the reaction product was analyzed by gas chromatography.

As a result, the conversion of succinic anhydride was 67.4%, the selectivity for GBL was 95.4%, and the yield of GBL was 64.3%.

EXAMPLES 14 and 15

The reaction was conducted in the same manner as in Example 13 except that instead of p-toluenesulfonic acid, other sulfonic acids were employed. The results are shown in Table 4.

TABLE 4

| | Sulfonic acid | | Formed GBL (mmol) | Conversion of succinic anhydride (%) | Selectivity for GBL (%) |
|---|---|---|---|---|---|
| | Type | Amount (mmol) | | | |
| Example 14 | Benzenesulfonic acid | 0.44 | 26.4 | 66.8 | 98.8 |
| Example 15 | Methanesulfonic acid | 0.44 | 24.2 | 69.3 | 87.3 |

EXAMPLE 16

The reaction was conducted in the same manner as in Example 13 except that instead of the ruthenium acetylacetonate, 0.011 g (0.025 mmol) of ruthenium acetate was used.

As a result, 21.4 mmol of GBL was obtained. The conversion of succinic anhydride was 56.0%, and the selectivity for GBL was 95.5%.

EXAMPLE 17

The reaction was conducted in the same manner as in Example 13 except that instead of the ruthenium acetylacetonate, 0.011 g (0.017 mmol) of dodecacarbonyltriruthenium was employed.

As a result, 18.4 mmol of GBL was obtained. The conversion of succinic anhydride was 51.3%, and the selectivity for GBL was 89.7%.

EXAMPLE 18

Into a bubble tower type SUS reactor, 0.0796 g (Ru: 0.2 mmol) of ruthenium acetylacetonate, 0.52 g (2.0 mmol) of triphenylphosphine, 0.25 g (1 mmol) of dodecylsulfonic acid, 20 ml of tetraglyme and, as the starting material for the reaction, 20.0 g (200 mmol) of succinic anhydride, were charged. While supplying hydrogen gas under normal pressure at a rate of 20 NTP liter/hr, the mixture was heated at 170° C. for 2 hours for reaction. As a result, 21 mmol of GBL was obtained.

EXAMPLE 19

Into a 200 ml induction agitation type autoclave equipped with a gas-liquid separator, 80 ml of tetraglyme was charged and the temperature was raised to 200° C. When the temperature reached 200° C., hydrogen was continuously supplied to the reactor under a pressure of 10 atm. at a flow rate of GHSV 460 hr$^{-1}$.

On the other hand, a starting material composition comprising 0.197% by weight of ruthenium acetylacetonate, 1.86% by weight of trioctylphosphine, 0.82% by weight of p-toluenesulfonic acid, 9.71% by weight of succinic anhydride and 87.41% by weight of tetraglyme, was continuously supplied to the reactor at a retention time of 1.6 hours. About 5 hours after the initiation of the reaction, the reaction product having a constant composition was obtained.

As the result of the reaction under the constant condition, the conversion of succinic anhydride was 93%, and the selectivity for GBL was 94%.

The reaction solution was heated at an oil bath temperature of 155° C. under a vacuum degree of 3 mmHg to distill off GBL, and then succinic anhydride was added to bring the composition to the above composition for the starting material, and the same reaction was repeated, whereby the conversion of succinic anhydride was 93%, and the selectivity for GBL was 99%.

COMPARATIVE EXAMPLE 3

(acid having a pKa of higher than 2)

Into a bubble tower type SUS reactor, 0.0769 g (Ru: 0.2 mmol) of ruthenium acetylacetonate, 0.74 g (2.0 mmol) of trioctylphosphine, 20 ml of tetraglyme and 2.15 g (2.0 mmol) of phosphoric acid (pKa=2.15) were charged, and, as the starting material for the reaction, 20.0 g (200 mmol) of succinic anhydride was charged. While supplying hydrogen gas under normal pressure at a rate of 10 NTP liter/hr, the mixture was heated at 200° C. for 4 hours for reaction, whereby no GBL formed.

EXAMPLE 20

Into a bubble tower type SUS reactor, 0.0796 g (Ru: 0.2 mmol) of ruthenium acetylacetonate, 0.74 g (2.0 mmol) of trioctylphosphine, 20 ml of tetraglyme and 0.380 g (2.0 mmol) of p-toluenesulfonic acid, were charged, and 20 ml of tetraglyme and, as the starting material for the reaction, 20.0 g (200 mmol) of succinic anhydride were charged. While supplying hydrogen gas under normal pressure at a rate of 10 NTP liter/hr, the mixture was heated at 200° C. for 4 hours for reaction.

As a result, the conversion of succinic anhydride was 20.5%, and the selectivity for GBL was 96.8%.

EXAMPLE 21

Into a SUS reactor, 0.0523 g (0.2 mmol) of trichlororutheniumhydrate, 0.371 g (1.4 mmol) of triphenylphosphine, 0.712 g (2.0 mmol) of sodium octadecylsulfonate ($C_{18}H_{37}SO_3Na$), 20 ml of tetraglyme and 20.0 g (200 mmol) of succinic anhydride were charged. While supplying hydrogen gas under normal pressure at a rate of 20 liter/hr, the mixture was heated at 170° C. for 2 hours for reaction. As a result, formed GBL was 42.0 mmol (yield: 21.0%), and hydrogenation products other than GBL were in a trace amount.

EXAMPLE 22

The reaction was conducted in the same manner as in Example 21 except that the triphenylphosphine was used in an amount of 1.43 g (5.4 mmol) and instead of sodium octadecylsulfonate, 0.272 g (1.0 mmol) of sodium dodecylsulfonate ($C_{12}H_{25}SO_3Na$) was used. As a result, formed GBL was 53.0 mmol (yield: 27.5%), and hydrogenation products other than GBL were in a trace amount.

COMPARATIVE EXAMPLES 4 to 10

(reaction system wherein an amine is added to a halogen-containing ruthenium complex)

Into a SUS reactor 0.002 g (0.01 mmol) of trichlororuthenium, 0.013 g (0.15 mmol) of triphenylphosphine, 0.1 mmol of an amine as identified in Table 5, 5 ml of tetraglyme and, as the starting material for the reaction, 1.0 g (10 mmol) of succinic anhydride, were charged. The reaction was conducted under a hydrogen pressure of 20 kG at 160° C. for 2 hours.

The results are shown in Table 5. It is evident from Table 5 that the reaction activity decreases by an addition of an amine.

TABLE 5

| | Amine | Yield of GBL (%) |
|---|---|---|
| Comparative Example 4 | None | 50.9 |
| Comparative Example 5 | Tributylamine | 5.0 |
| Comparative Example 6 | Tetramethylethylenediamine | Trace |
| Comparative Example 7 | 2-Hydroxypyridine | 34.8 |
| Comparative Example 8 | Phenanthroline | Trace |
| Comparative Example 9 | Pyridine | 22.1 |
| Comparative Example 10 | Diazabicycloundecene-7 | 3.0 |

According to the present invention, for the production of a lactone by hydrogenating a dicarboxylic acid, a dicarboxylic acid anhydride and/or a dicarboxylic ester, the reaction is conducted in a homogeneous liquid phase reaction by using the ruthenium catalyst of the present invention as the catalyst, whereby the desired product can be obtained at high selectivity under a mild condition as compared with the conventional methods.

The catalyst of the present invention is excellent in the stability of its activity, and no substantial deterioration of the conversion is observed even when used for a long period of time, whereby the desired product can be obtained at high selectivity over a long period of time.

What is claimed is:

1. A method for producing a lactone by hydrogenating a dicarboxylic acid, a dicarboxylic acid anhydride and/or a dicarboxylic acid ester in the presence of a catalyst, wherein said catalyst is a ruthenium catalyst comprising (1) ruthenium, (2) an organic phosphine and (3) a conjugate base of an acid having a pKa of less than 2, selected from the group consisting of Brønsted acids including p-toluenesulfonic acid, trifluoromethanesulfonic acid, nitric acid, benezensulfonic acid, methanesulfonic acid, dodecylsulfonic acid and octadecylsulfonic acid, and alkali metal salts, alkali earth metal salts, ammonium salts and silver salts of these Bronsted acids.

2. The method according to claim 1, wherein the ruthenium catalyst further contains (4) a neutral ligand.

3. The method according to claim 1, wherein the molar ratio of (1) the ruthenium : (2) the organic phosphine : (3) the conjugate base of an acid having a pKa of less than 2 is 1 : 0.1–1,000 : 0.01–1,000.

4. The method according to claim 1, wherein the molar ratio of (1) the ruthenium : (2) the organic phosphine : (3) the conjugate base of an acid having a pKa of less than 2 is 1 : 1–100 : 0.1–100.

5. The method according to claim 1, wherein the conjugate base of an acid having a pKa of less than 2 is a p-toluenesulfonic acid anion.

6. The method according to claim 1, wherein the conjugate base of an acid having a pKa of less than 2 is a trifuloromethanesulfonic acid anion.

7. The method according to claim 1, wherein the conjugate base of an acid having a pKa of less than 2 is a nitric acid anion, a methanesulfonic acid anion, an octadecylsulfonic acid anion or a dodecylsulfonic acid anion.

* * * * *